United States Patent [19]

Watanabe et al.

[11] Patent Number: 4,701,267
[45] Date of Patent: Oct. 20, 1987

[54] METHOD FOR REMOVING LEUKOCYTES

[75] Inventors: Hiroyuki Watanabe; Hiroshi Rikumaru, both of Oita, Japan

[73] Assignee: Asahi Medical Co., Ltd., Tokyo, Japan

[21] Appl. No.: 711,667

[22] Filed: Mar. 14, 1985

[30] Foreign Application Priority Data

Mar. 15, 1984 [JP] Japan .................................. 59-48173
Mar. 27, 1984 [JP] Japan .................................. 59-57450

[51] Int. Cl.$^4$ ...................... B01D 27/02; B01D 36/02; B01D 39/02
[52] U.S. Cl. .................................. 210/806; 210/335; 210/491; 210/492; 210/505
[58] Field of Search ............... 210/335, 446, 451, 489, 210/491, 492, 927, 767, 806, 295, 319, 504, 503, 505, 508, 509; 55/512, 527

[56] References Cited

U.S. PATENT DOCUMENTS

| | | | |
|---|---|---|---|
| 3,003,643 | 10/1961 | Thomas | 210/491 |
| 4,009,715 | 3/1977 | Forberg et al. | 210/927 X |
| 4,073,732 | 2/1978 | Lauer et al. | 210/491 |
| 4,191,654 | 3/1980 | Larson | 210/927 X |
| 4,229,306 | 10/1980 | Hein et al. | 210/927 X |
| 4,246,107 | 1/1981 | Takenaka et al. | 210/927 X |
| 4,283,289 | 8/1981 | Meyst et al. | 210/450 X |
| 4,294,594 | 10/1981 | Sloane, Jr. et al. | 210/927 X |
| 4,330,410 | 5/1982 | Takenaka et al. | 210/927 X |
| 4,342,730 | 8/1982 | Perrotta | 210/509 X |
| 4,376,675 | 3/1983 | Perrotta | 210/509 X |
| 4,608,173 | 8/1986 | Watanabe et al. | 210/508 X |

Primary Examiner—Richard V. Fisher
Assistant Examiner—W. Gary Jones
Attorney, Agent, or Firm—Birch, Stewart, Kolasch and Birch

[57] ABSTRACT

A filter unit for removing leukocytes from a leukocyte-containing suspension, comprising a container provided with at least one inlet conduit means and at least one outlet conduit means, the container having a main filter packed therein in the form of a non-woven fabric which comprises fibers of an average diameter of from 0.3 μm to less than 3 μm and which has a bulk density of from 0.01 g/cm³ to 0.7 g/cm³, and which has an average distance between two adjacent fibers defined by the following equation (1) of from 0.5 μm to 7.0 μm:

$$y = x\left(\sqrt{\frac{\pi}{2\sqrt{3}} \cdot \sqrt{\frac{\rho}{D}}} - 1\right) \tag{1}$$

wherein y is the average distance between two adjacent fibers in micron; x is the average diameter of fibers in microns; $\rho$ is the density of the fibers in g/cm³; D is the bulk density of the filter in g/cm³; and $\pi$ is a circular constant.

2 Claims, 6 Drawing Figures

FIG. 1
FIG. 2
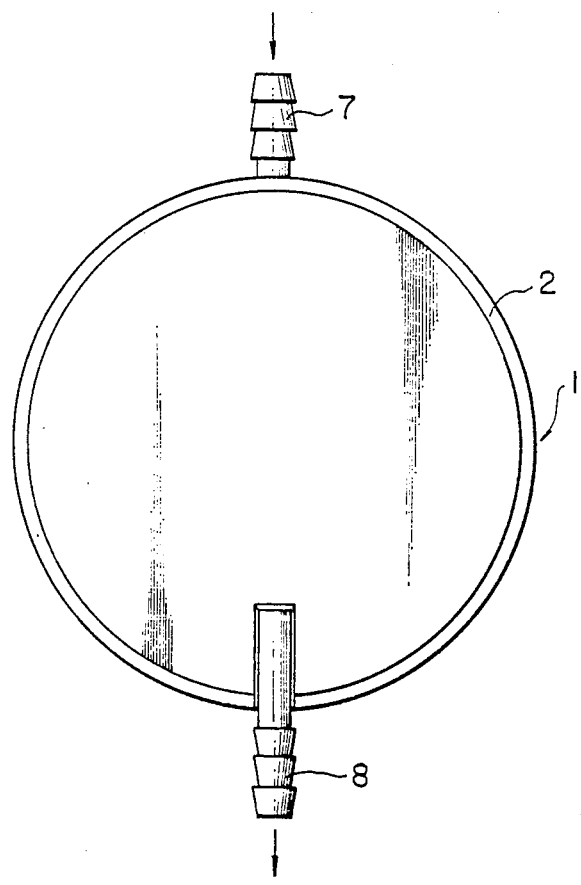
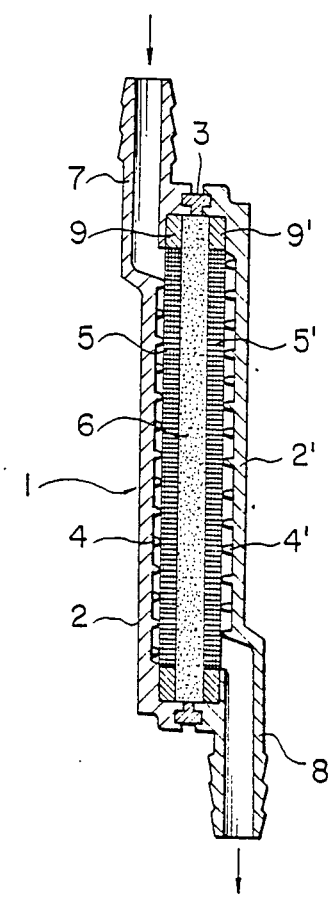

FIG.3
FIG.4
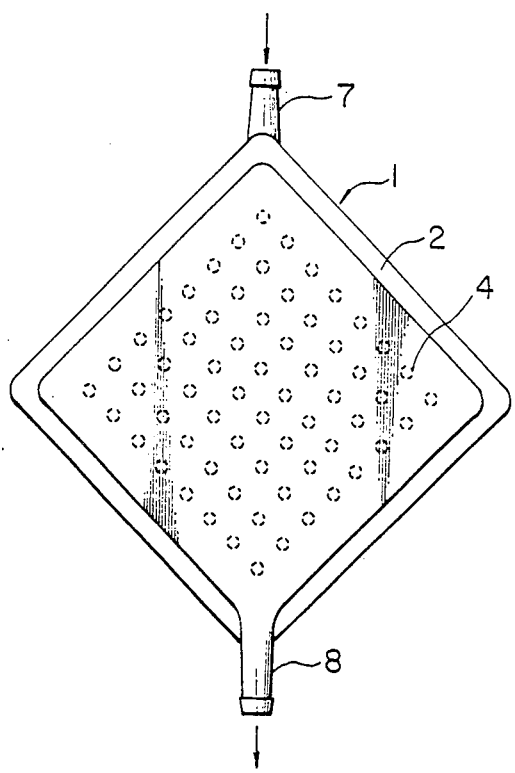
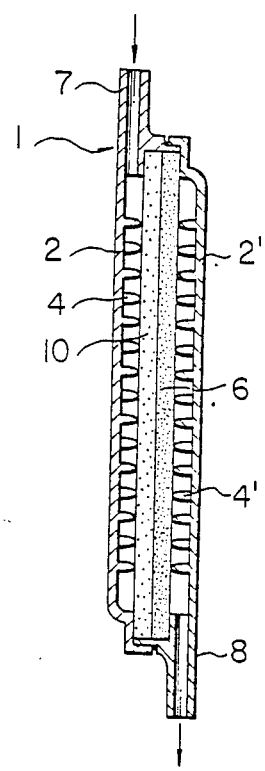

METHOD FOR REMOVING LEUKOCYTES

DESCRIPTION OF THE PRIOR ART

In recent years component transfusions have often been employed in place of whole blood transfusions. Component transfusions involve transfusing particular blood components needed or desired for the patients and separated from unneeded or injurious components. Particularly, erythrocyte transfusions for the patients of anemia, heart-disease, or lung disease are now in frequent use. In an erythrocyte suspension prepared for the erythrocyte transfusion, leuckocytes should be removed from erythrocyte suspension as much as possible. Histocompatibility antigens in leukocytes of transfusion-donors may generate anti-leukocyte antibodies in the blood of transfusion-receivers, or graft versus host (GVH) reaction may occur due to imcompatibility of the histocompatibility antigens in transfusion-receivers, and as a result, transfusion receivers may suffer from side-effects such as a rigor, a fever, a headache and nausea.

Various processes have been employed for the removal of leukocytes from leukocyte-containing suspensions. Typical processes to provide leukocyte-poor blood include a centrifugation process, an agglutinant incorporation-sedimentation process, and a filtration process. The centrifugation process involves separating blood into plasma, leukocyte, platelets and erythrocytes taking advantage of the difference of respective densities. This centrifugation process has several disadvantages in that it needs very expensive apparatus, it requires repeated washing of centrifuged leukocyte-poor suspensions with a physiological salt solution and approximately 20% of centrifuged leukocyte-poor suspensions is wasted when erythrocyte components are collected to obtain leukocyte-poor suspensions. The agglutinant incorporation-sedimentation process involves incorporating an erythrocyte agglutinant such as dextran with blood, then subjecting the agglutinant incorporated suspension to sedimentation to separate the blood into an erythrocyte sediment and a leukocyte-and-platelet containing plasma layer. This process also has a disadvantage in that it requires repeated washing of the resulting erythrocyte suspensions with a physiological salt solution to obtain leukocyte-poor suspensions, and this washing takes much time and is a very troublesome operation.

The filtration process involves passing blood through a filter composed of a leukocyte-adherent material which does not alter blood components thereby entrapping leukocytes in the filter, and then collecting leukocyte-poor suspensions passed through the filter. This process has an advantage in that leukocyte-poor suspensions can easily be obtained at a high yield from blood. The conventional leukocyte filtering apparatus for separating and recovering an leukocyte composition shown in U.S. Pat. No. 4,330,410 (or GB No. 2018151A) comprises a column having a mass of fibers packed therein with an average diameter of from 3.0 $\mu$m to 10 $\mu$m in a bulk density of from 0.02 g/cm$^3$ to 0.40 g/cm$^3$. This column is capable of separating leukocytes from erythrocyte suspension easily and at a high efficiency. However, this conventional apparatus is not suitable for treating a considerable amount of the blood, for example, more than 200 ml, which amount is usually treated in medical facilities, because it takes too much time and leukocytes are not sufficiently removed from the leukocyte-containing suspension.

SUMMARY OF THE INVENTION

A main object of the invention is to provide a filter unit for removing leukocytes from blood in a simple operation and within a short period of time. The filter unit of the present invention can remove leukocytes from a leukocyte-containing suspension in an enhanced purity.

In accordance with the present invention, there is provided a filter unit for removing leukocytes from a leukocyte-containing suspension, comprising a container provided with at least one inlet conduit means and at least one outlet conduit means, the container having a main filter packed therein in the form of a non-woven fabric, which main filter comprises fibers of an average diameters of from 0.3 $\mu$m to less than 3 $\mu$m, and has a bulk density of from 0.01 g/cm$^3$ to 0.7 g/cm$^3$, and has an average distance between two adjacent fibers defined by the following equation (1) of from 0.5 $\mu$m to 7.0 $\mu$m:

$$y = x \left( \sqrt{\frac{\pi}{2\sqrt{3}}} \cdot \sqrt{\frac{\rho}{D}} - 1 \right) \tag{1}$$

wherein y is the average distance between two adjacent fibers in $\mu$m; x is the average diameter of the fibers in $\mu$m; $\rho$ is the density of the fibers in g/cm$^3$; D is the bulk density of the filter in g/cm$^3$; and $\pi$ is a circular constant.

The present invention also provides a filter unit for removing leukocytes from the blood bank blood which has storage-generated microaggregates and adhesive substances therein, which filter unit comprises a container provided with at least one inlet conduit means and at least one outlet conduit means, and the container having a prefilter and the above described main filter packed therein.

BRIEF DESCRIPTION OF THE DRAWINGS

In the drawings:

FIG. 1 shows an embodiment of the filter unit of this invention;

FIG. 2 is a view of the side section of the filter unit shown in FIG. 1;

FIG. 3 shows another embodiment of the filter unit of this invention;

FIG. 4 is a view of the side section of the filter unit shown in FIG. 3;

DESCRIPTION OF THE PREFERRED EMBODIMENTS

Figure 5:
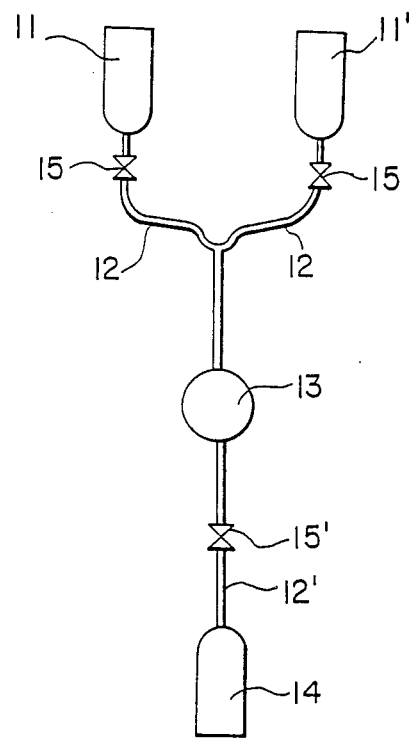
FIG. 5 shows an embodiment of the blood treating apparatus employed in this invention.

The filter unit of the present invention has at least one main filter in a container, and may also have a prefilter being placed on the main filter, if necessary.

The container in which the main filter and, if necessary, the prefilter are to be packed may be of any inner shape provided that the container has at least one inlet conduit and at least one outlet conduit through which the blood can be introduced into and withdrawn from the container, respectively. It is preferable, that however, that the inner shape of the container is that of a flat column, for example, a flat polygon or a flat cylindrical shape in view of efficiency of filtration.

The fibers to be packed in the container of the filter unit as a main filter are selected from synthetic fibers, semi-synthetic fibers, regenerated fibers and inorganic fibers. One of these types of fibers may be used by itself or a combination of the different types of fibers may be used. The synthetic fibers made of polymers such as polyester, polyamide, polyacrylonitrile, polyethylene, polypropylene, polymethyl-methacrylate, polystyrene and polyfluorochloroethylene are preferably used in the main filter. The fibers have an average diameters of from 0.3 μm to less than 3 μm, and these fibers may be produced, for example, by the melt-blowing process, but the method for spinning these fibers is not limited to the melt-blowing process.

The term "average diameter of fibers" used herein is defined by the following equation (2):

$$x = 2\sqrt{\frac{w}{\pi \cdot \rho \cdot l}} \cdot 10^4 \quad (2)$$

wherein x is an average diameter of the fibers in μm; w is a weight of the fiber in gram; $\pi$ is a density of the fibers in g/cm$^3$; and l is a length of the fibers in cm.

If the average diameter of the fibers is not less than 3 μm, leukocytes hardly adhere to the fibers and the main filter consisting of such fibers can hardly entrap and remove leukocytes. On the other hand, when the average diameter of the fibers is less than 0.3 μm, mechanical strength of the fibers is so low that the fibers are apt to be destroyed, and as a result such fine fibers may injure erythrocytes and cause hemolysis. Further, these fine fibers must be packed densely into a container of the filter unit in order to provide a stable main filter in which a mass of fibers is uniformly packed in any portion of the filter, therefore the average distance between two adjacent fibers may become too narrow for erythrocytes, let alone for leukocytes, to pass therethrough, and thus the filter may be clogged.

According to the present invention, the main filter is in the form of a non-woven fabric, and preferably in the form of entangled or interlaced fibers. In order to obtain the non-woven fabric, the fibers are entangled mutually only by blowing air or high-pressured steam on a mass of fibers and bonding the fibers with one another. The non-woven fabric may also be formed by entangling and bonding the fibers by heat or with an adhesive.

In the non-woven fabric, the fibers are oriented and arranged perpendicular to the filtration flow of the blood, and therefore the main filter becomes thin in the direction parallel to the filtration flow of blood. Thin filters have such advantages that the pressure drop of the blood in passing through the filter is low and the time required for treating a certain amount of blood can be shortened. The main filter in the form of a non-woven fabric can prevent channeling of the blood when the blood is passed through because distances between two adjacent fibers are almost identical and moderately narrow in any portion of the filter. The filter in the form of a non-woven fabric has another advantage that it never emits thrum of fibers which is deleterious for blood in spite of fineness of the fibers used, and accordingly it is suitable for blood treating.

The bulk density of the non-woven fabric as a main filter is from 0.001 g/cm$^3$ to 0.7 g/cm$^3$ and preferably from 0.10 g/cm$^3$ to 0.5 g/cm$^3$. The term "bulk density" used herein means a numerical value expressed in g/cm$^3$ obtained by dividing the weight (in gram) of the mass of fibers by the volume (in cm$^3$) of the mass of fibers. If the bulk density of the above described non-woven fabric is less than 0.01 g/cm$^3$, leukocytes may leak in passing through the non-woven fabric as a main filter when blood is treated at a considerably high flow rate so as to shorten the time required for the blood treating. On the other hand, if the bulk density of the non-woven fabric is more than 0.7 g/cm$^3$, the non-woven fabric as a main filter may entrap not only leukocytes but also erythrocytes due to the too narrow distance between the fibers constituting the non-woven fabric.

Figure 6:
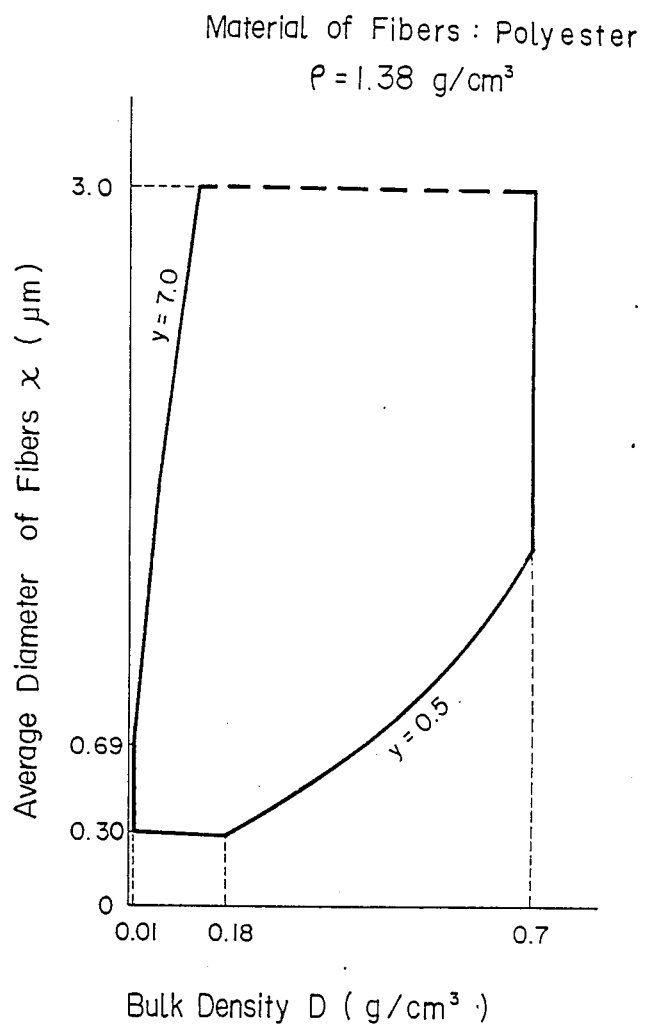
FIG. 6 is a graph showing the relationship between the average diameter of the fibers and the bulk density in the case of polyester fibers.

Taking the case of polyester fibers, the relation of the average diameter of fibers x and the bulk density of the filter D is shown in FIG. 6. The region surrounded by the solid line and the solid-broken line in FIG. 6 provides the above described relation, provided that the solid line in FIG. 6 is included, while the solid-broken line in FIG. 6 is excluded in the present invention. In FIG. 6, y is the average distance between two adjacent fibers defined by the equation (1).

When the main filter in a non-woven fabric form is manufactured, suitable average diameters and densities of the fibers used therein and suitable bulk densities of the non-woven fabric should be selected in such a range that the average distance between two adjacent fibers defined by the equation (1) is from 0.5 μm to 7 μm. When the average distance between two adjacent fibers is less than 0.5 μm, it is difficult for erythrocytes to pass through the distance between two adjacent fibers. Conversely if the distance is more than 7 μm, the filter must be made bulky in order to entrap leukocytes in the filter.

The thickness of the non-woven fabric as a main filter in the direction of the filtration flow is typically from 1 mm to 30 mm, preferably from 1 mm to 20 mm, and more preferably from 1.5 mm to 10 mm in order to treat blood in a short period of time. If the thickness of the main filter is smaller than 1 mm, the filter cannot entrap leukocytes sufficiently. On the contrary, if the thickness is larger than 30 mm, the pressure drop of the blood in passing through the mentioned filter becomes too much high.

The area of the surface of the main filter at the inlet-side in a container of the filter unit is typically from 10 cm$^2$ to 2000 cm$^2$, preferably 20 cm$^2$ to 1000 cm$^2$, and more preferably 25 cm$^2$ to 300 cm$^2$ for treating approximately 500 ml of blood. If the area is too small for the amount of blood to be treated, the surface of the main filter facing the inlet conduit in a container of the filter unit may be saturated with entrapped leukocytes as soon as the treating of the blood is started, and the filtering speed may reduce immediately. If the area is too large, erythrocytes may be apt to be retained between the fibers in the filter and it is very difficult and troublesome to recover those erythrocytes, and as a result, the recovery of erythrocytes decreases.

According to the present invention, it is preferred when the blood which has been stored for a long period of time and which has the storage-generated microaggregates and adhesive substances therein is treated, that a prefilter may be used together with the above described main filter.

It has been discovered that when blood bank blood is stored, blood components are altered, and microaggregates consisting of platelets, fibrin, leukocytes, etc. and adhesive substances consisting of fibrin, protein-gel, etc. are produced in the blood. These aggregates grow with more prolonged blood storage.

When the blood having such aggregates therein is treated by the filter unit which has only the main filter as described above in a container as described above, the main filter is likely clogged with the aggregates and the filter unit cannot perform its essential function.

The prefilter may be composed of either one type of filter or a laminate of various types of filters, and the prefiler may preferably be in the form of a woven or non-woven fabric of fibers selected from synthetic fibers, semi-synthetic fibers, regenerated fibers, inorganic fibers and natural fibers. These fibers, however may be allowed to be packed in a container as it is. The fibers used for the prefilter have an average diameters of from 3 $\mu$m to 60 $\mu$m, preferably from 4 $\mu$m to 40 $\mu$m, and an average distance between two adjacent fibers defined by the equation (1) of preferably from 7 $\mu$m to 300 $\mu$m. A prefilter which is constituted of the fibers having an average diameter of less than 3 $\mu$m and which has an average distance between two adjacent fibers of less than 7 $\mu$m has so narrow a distance between two adjacent fibers that the storage-generated microaggregates and adhesive substances may cause clogging on and in the prefilter. Conversely, a prefilter which is constituted of the fibers having an average diameter of more than 60 $\mu$m and which has an average distance between two adjacent fibers of more than 300 $\mu$m has so wide a distance between two adjacent fibers that the storage-generated microaggregates and adhesive substances cannot be entrapped by the prefilter at all.

When the prefilter is constituted by laminating different types of filters in average diameter of the fibers and/or average distance between two adjacent fibers, these filters may preferably be laminated in the order from the filter which has larger average diameter of the fibers and/or larger average distance between two adjacent fibers toward downstream of filtration flow. When the prefilter is constituted by laminating different type of filters in material of fibers, the filter consisting of hydrophilic fibers and the filter consisting of hydrophobic fibers may preferably be laminated interchangeably.

The thickness of the prefilter is from 0.1 mm to 30 mm, preferably from 0.5 mm to 20 mm, more preferably 1 mm to 10 mm, considering even balance among the filtration ability of the prefilter, the filtration efficiency and the pressure drop of blood passing through the prefilter.

It is preferred that the area of the surface of the prefilter at the inlet-side in a container of the filter unit is preferably almost the same as that of the main filter, considering the filtration efficiency.

In FIGS. 1 and 2, a container 1 of the filter unit is constructed with a flat wall 2 having an inlet conduit 7, a flat wall 2' having an outlet conduit 8, and a frame 3. In FIGS. 3 and 4, a container 1 of the filter unit is constructed with a flat wall 2 having an inlet conduit 7, and a flat wall 2' having an outlet conduit 8. The flat walls 2 and 2' have many tubercles 4 and 4' which are arranged in neat order on the inside of the walls 2 and 2', respectively. In the filter unit which is shown in FIGS. 1 and 2, a main filter 6 is held between mesh type supports 5 and 5', and further put between tubercles 4 and 4'. The periphery of the main filter 6 is fixed to the container by packings 9 and 9'. In the filter unit which is shown in FIGS. 3 and 4, a prefilter 10 and a main filter 6 are laminated, and they are fixed in a container 1 in being put between tubercles 4 and 4'.

The fresh blood flows into the filter unit shown in FIGS. 1 and 2 through the inlet conduit 7, overspreads in the space among the wall 2 and the support 5 and the tubercles 4, and passes through the support 5, the main filter 6, and the support 5' in this order, and then the blood flows in the space among the tubercles 4' and flows out through the outlet conduit 8. When the fresh blood passes through the main filter 6, leukocyte components are entrapped by the main filter 6. The stored blood flowing into the filter unit shown in FIGS. 3 and 4 through the inlet conduit 7 overspreads to the space between the wall 2 and the tubercles 4, and passes through the prefilter 10 and the mainfilter 6, and then the blood flows in the space among the tubercles 4' and flows out through the outlet conduit 8. When the stored blood passes through the prefilter 10, the storage-generated platelet leukocyte aggregates present in the stored blood are entrapped by the prefilter 10, and when the stored blood from which the storage-generated microaggregates and adhesive substances have just been removed passes through the main filter 6, leukocyte components are entrapped by the main filter 6.

A filter unit 13 is assembled as a blood filtering apparatus shown in FIG. 5. Blood bags 11 and 11' and the filter unit 13 and a bag for recovering the filtrate blood 14 are joined vertically in this order by tubes 12 and 12'. The tube 12 between the blood bags and the filter unit 13, and the tube 12' between the filter unit 13 and the bag 14 have valves 15 and 15', respectively. The treating blood in the blood bags 11 and 11' flows down through tubes 12 and flows into the filter unit 13, where the treating blood is separated, and the filtrate, i.e. the erythrocyte suspension passes through the filter unit 13 and flows down through the tube 12', and then is collected in the bag 14.

The blood to be treated can be introduced into the filter unit of the present invention by using a blood pump, as well as by means of gravity as described above.

By using the filter unit of the present invention, leukocytes can be removed in a simple operation and within a short period of time.

The invention will be further illustrated by the following examples. However, it should be understood that the invention is in no way limited by these examples.

In the examples, percentages of the removal rate of leukocytes and the recovery rate of erythrocytes are shown by numbers of blood cells. Further, the effective diameter of a filter is determined by measuring the diameter of the filter where blood can actually flow. In the following examples except Example 8 and Comparative Example 7, two mesh type sheets each having a thickness of 2 mm are used as shown in FIG. 2.

EXAMPLE 1

A non-woven fabric having a bulk density of 0.18 g/cm$^3$ and an average distance between two adjacent fibers of 2.0 $\mu$m was prepared by spinning polyester fibers having a density of 1.38 g/cm$^3$ and an average diameter of 1.2 $\mu$m by the melt-blowing process, and entangling the fibers. A filter unit was prepared by cutting out the non-woven fabric in the form of a disk having a diameter of 110 mm and a thickness of 7 mm to obtain a filter, and fixing the filter in a container provided with an inlet conduit and an outlet conduit and having an inside thickness of 11 mm. The effective diameter of the filter was 100 mm.

A blood treating apparatus was assembled by placing the filter unit under two 300 ml blood bags at the distance of 800 mm below, connecting the filter unit and the blood bags by tubes having an inner diameter of 3 mm and an outer diameter of 5 mm, placing 1l bag for collecting the treated blood at the distance of 800 mm below from the filter unit, and connecting the filter unit and the bag by the same tube as described above.

To each of the blood bags of the blood treating apparatus was fed 250 ml of CPD solution (citrate-phosphate-dextrose)-added A type fresh whole blood (hematocrit: 38%) from a healthy donor. Then, all the blood was allowed to flow through the filter unit from one of the blood bags and then the other at 25 °C. by gravity caused by the head. Then, 90 ml of a physiological saline was added and flowed by gravity to recover erythrocytes remaining in the filter unit.

It took 6 minutes and 35 seconds for 500 ml of the fresh blood to flow through the filter unit, and thus the flow rate was 76 ml/min. The removal rate of leukocytes was 99.7% and the recovery rate of erythrocytes was 95%.

COMPARATIVE EXAMPLE 1

9 g of polyester fibers (density: 1.38 g/cm$^3$) having an average diameter of 9.6 $\mu$m and a length of from 40 to 70 mm were uniformly packed at a bulk density of 0.13 g/cm$^3$ into a cylindrical column having a diameter of 30 mm and a length of 100 mm, thereby to prepare a leukocyte removing filter. The average distance between two adjacent fibers was 20.2 $\mu$m.

A blood treating apparatus was assembled in the same manner as in Example 1 except that the leukocyte removing filter was used instead of the filter unit.

The blood treating procedures of Example 1 were repeated except that 80 ml of a physiological saline was used instead of 90 ml of the physiological saline.

As a result, it took one hour and 32 minutes and 35 seconds for 500 ml of the fresh blood to flow through the filer, and thus the flow rate was 5.4 ml/min. The removal rate of leukocytes was 93.2% and the recovery rate of erythrocytes was 93%.

EXAMPLE 2

A non-woven fabric having a bulk density of 0.22 g/cm$^3$ and an average distance between two adjacent fibers of 2.5 $\mu$m was prepared by sprinning polyester fibers having a density of 1.38 g/cm$^3$ and an average diameter of 1.8 $\mu$m by the melt-blowing process, and entangling the fibers. A filter unit was prepared by cutting out the non-woven fabric in the form of a disk having a diameter of 78 mm and a thickness of 4 mm to obtain a filter, and fixing the filter in a container provided with an inlet conduit and an outlet conduit and having an inside thickness of 8 mm. The effective diameter of the filter was 68 mm.

By using the filter unit, a blood treating apparatus was assembled in the same manner as in Example 1.

To each of the two blood bags of the blood treating apparatus was fed 250 ml of ACD-A solution (acid-citrate-dextrose)-added B type fresh whole blood (hematocrit: 42%) from a healthy donor. Then, all the blood was allowed to flow through the filter unit from one of the blood bags and then the other at 25° C. by gravity caused by the head. Subsequently, 40 ml of a physiological saline was added and flowed by gravity to recover erythrocytes remaining in the filter unit.

It took 7 minutes and 15 seconds for 500 ml of the fresh blood to flow through the filter unit, and thus the flow rate was 69 ml/min. The removal rate of leukocytes was 100% and the recovery rate of erythrocytes was 98%.

COMPARATIVE EXAMPLE 2

6.6 g of polyamide fibers (nylon 66) having an average diameter of 7.2 $\mu$m and a length of from 40 to 70 mm (density: 1.14 g/cm$^3$) were uniformly packed at a bulk density of 0.093 g/cm$^3$ into a cylindrical column having a diameter of 36 mm and a length of 70 mm, thereby to prepare a leukocyte removal filter. The average distance between two adjacent fibers was 16.8 $\mu$m.

A blood treating apparatus was assembled in the same manner as in Example 2 except that the leukocyte removing filter was used instead of the filter unit.

The blood treating procedures of Example 2 were repeated except that 80 ml of a physiological saline was used instead of 40 ml of the physiological saline.

As a result, it took one hour and 24 minutes and 45 seconds for 500 ml of the fresh blood to flow through the filter, and thus the flow rate was 5.9 ml/min. The removal rate of leukocytes was 95.1% and the recovery rate of erythrocytes was 94%.

EXAMPLE 3

A non-woven fabric having a bulk density of 0.16 g/cm$^3$ and an average distance between two adjacent fibers of 1.2 $\mu$m was prepared by spinning polyamide fibers (nylon 66) having a density of 1.14 g/cm$^3$ and an average diameter of 0.8 $\mu$m by the melt-blowing process, and entangling the fibers. A filter unit was prepared by cutting out the non-woven fabric in the form of a disk having a diameter of 100 mm and a thickness of 2 mm to obtain a filter, and fixing the filter in a container provided with an inlet conduit and an outlet conduit and having an inside thickness of 6 mm. The effective diameter of the filter was 90 mm.

By using the filter unit, a blood treating apparatus was assembled in the same manner as in Example 1.

To each of the two blood bags of the blood treating apparatus was fed 250 ml of CPD solution-added A type fresh whole blood (hematocrit: 45%) from a healthy donor. Then, all the blood was allowed to flow through the filter unit from one of the blood bags and then the other at 25° C. by gravity caused by the head. Subsequently, 50 ml of a physiological saline was added and flowed by gravity to recover erythrocytes remaining in the filter unit.

It took 6 minutes and 29 seconds for 500 ml of the fresh blood to flow through the filter unit, and thus the flow rate was 77 ml/min. The removal rate of leukocytes was 99.9% and the recovery rate of erythrocyteds was 98%.

COMPARATIVE EXAMPLE 3

18 g of acrylic fibers (density: 1.28 g/cm$^3$) having an average diameter of 5.2 $\mu$m and a length of from 40 to 70 mm were uniformly packed at a bulk density of 0.090 g/cm$^3$ into a cylindrical column having a diameter of 80 mm and a length of 40 mm, thereby to prepare a leukocyte removing filter. The average distance between two adjacent fibers of 13.5 $\mu$m.

A blood treating apparatus was assembled in the same manner as in Example 3 except that the leukocyte removing filter was used instead of the filter unit.

The blood treating procedures of Example 3 were repeated except that 210 ml of a physiological saline was used instead of 50 ml of the physiological saline.

As a result, it took 19 minutes and 14 seconds for 500 ml of the fresh blood to flow through the filter, and thus the flow rate was 26 ml/min. The removal rate of leukocytes was 68.4% and the recovery rate of erythrocytes was 91.3%.

EXAMPLE 4

A non-woven fabric having a bulk density of 0.28 g/cm$^3$ and an average distance between two adjacent fibers of 3.1 μm was prepared by spinning polyester fibers having a density of 1.38 g/cm$^3$ and an average diameter of 2.8 μm by the melt-blowing process, entangling the fibers, and heating the entangled fibers at 250° C. for 2 seconds for bonding the contact points of the fibers.

A filter unit was prepared by cutting out the non-woven fabric in the form of a disk having a diameter of 160 mm and a thickness of 8 mm, and fixing the fabric in a container provided with an inlet conduit and an outlet conduit, and having an inside thickness of 12 mm. The effective diameter of the filter was 150 mm.

By using the filter unit, a blood treating apparatus was assembled in the same manner as in Example 1.

CPD solution-added O type blood from a healthy donor was centrifuged to remove a small amount of plasma, thereby to prepare concentrated blood having a hematocrit of 64%. The concentrated blood was stored for one day at 4° C., and to each of the two blood bags of the blood treating apparatus was fed 200 ml of the blood. Immediately, the blood was allowed to flow through the filter unit from one of the blood bags and then the other at 10° C. by gravity caused by the head. Subsequently, 220 ml of a physiological saline was added and flowed by gravity to recover erythrocytes remaining in the filter unit. It took 6 minutes and 27 seconds for 400 ml of the fresh blood to flow through the filter unit, and thus the flow rate was 62 ml/min. The removal rate of leukocytes was 98.9% and the recovery rate of erythrocytes was 91%.

EXAMPLE 5

A thermally bonded non-woven fabric having a bulk density of 0.31 g/cm$^3$ (average distance between two adjacent fibers: 12.1 μm) and composed of polyester fibers having a density of 1.38 g/cm$^3$ and an average diameter of 12 μm was cut out in the form of a disk having a diameter of 110 mm and a thickness of 1.2 mm, thereby to prepare a prefilter for removing altered blood components.

A non-woven fabric having a bulk density of 0.16 g/cm$^3$ and an average distance between two adjacent fibers of 1.8 μm was prepared by spinning polyester fibers having an average diameter of 1.0 μm and a density of 1.38 g/cm$^3$ by the melt-blowing process, and entangling the fibers. Then, the non-woven fabric was cut out in the form of a disk having a diameter of 110 mm and a thickness of 2.0 mm, thereby to prepare a main filter for entrapping and removing leukocytes.

A filter unit was prepared by placing the prefilter on the main filter, and fixing the piled filters in a container provided with an inlet conduit and an outlet conduit and having an inside thickness of 8 mm so as to face the prefilter to the inlet conduit and the main filter to the outlet conduit, respectively. The effective diameter of the filters was 100 mm.

By using the filter unit, a blood treating apparatus was assembled in the same manner as in Example 1.

To each of the two blood bags of the blood treating apparatus was fed 200 ml of CPD solution-added O type whole blood (hematocrit: 41%) from a healthy donor, and was stored for 8 days. Then, all the blood was allowed to flow through the filter unit from one of the blood bags and then the other at 25° C. by gravity caused by the head. Subsequently, 70 ml of a physiological saline was added and flowed by gravity to recover erythrocytes remaining in the filter unit.

It took 5 minutes and 29 seconds for 400 ml of the stored blood to flow through the filter unit, and thus the flow rate was 73 ml/min. The number of microaggregates of altered blood components at least 15 μm in size was 4,300 in 1 milliliter of the filtrate while the average number of the microaggregates contained in the stored blood in the two blood bags had been 1.07 × 10$^6$ per milliliter. Thus, the removal rate of microaggregates was 99.6%. The removal rate of leukocytes was 98.8% and the recovery rate of erythrocytes was 94%.

COMPARATIVE EXAMPLE 4

A filter unit was prepared in the same manner as in Example 5 except that the prefilter was not used and the inside thickness of the container was 6 mm.

A blood treating apparatus was assembled in the same manner as in Example 5 by using the filter unit without the prefilter instead of the filter unit of Example 5.

To each of the two blood bags of the blood treating apparatus was fed 200 ml of the same stored blood as the one used in Example 5. Then, the blood was fed into the filter unit from one of the blood bags and then the other at 25° C. by gravity caused by the head. After one hour and 20 minutes from the starting of the filtration and when 319 ml of the blood was fed into the filter unit, no filtrate could be obtained due to the clogging of altered blood components contained in the stored blood.

EXAMPLE 6

A thermally bonded non-woven fabric having a bulk density of 0.14 g/cm$^3$ (average distance between two adjacent fibers: 58 μm) and composed of polyester fibers having an average diameter of 29 μm was cut out in the form of a disk having a diameter of 78 mm and a thicknes of 3.0 mm. This disk is referred to prefilter I hereinafter.

A thermally bonded non-woven fabric having a bulk density of 0.18 g/cm$^3$ (average distance between two adjacent fibers: 26.2 μm) and composed of cuprammonium regenerated cellulose fibers having a density of 1.50 g/cm$^3$ and an average diameter of 15 μm was cut out to two disks each having the same diameter of 78 mm and a thickness of 2.0 mm and 0.65 mm. These disks are referred to as prefilters II and IV, respectively, hereinafter.

A thermally bonded non-woven fabric having a bulk density of 0.31 g/cm$^3$ (average distance between two adjacent fibers: 12.1 μm) and composed of polyester fibers having a density of 1.38 g/cm$^3$ and an average diameter of 12 μm was cut out to two disks each having a diameter of 78 mm and a thickness of 0.6 mm. These disks are referred to as prefilter III and prefilter V, respectively, hereinafter.

A non-woven fabric having a bulk density of 0.23 g/cm$^3$ and an average distance between two adjacent fibers of 2.4 μm was prepared by spinning polyester fibers having an average diameter of 1.8 μm and a density of 1.38 g/cm$^3$ by the melt-blowing process, and entangling the fibers. Then, the non-woven fabric was cut out in the form of a disk having a diameter of 78 mm and a thickness of 4 mm, thereby to prepare a main filter for entrapping and removing leukocytes.

A filter unit was prepared by piling the main filter and the prefilters V, IV, III, II and I on one another in this order, and fixing the piled filters in a container provided with an inlet conduit and an outlet conduit and having an inside thickness of 15 mm so as to face the prefilter I to the inlet conduit and the main filter to the outlet conduit, respectively. The effective diameter of the filters was 68 mm.

A blood treating apparatus was assembled in the same manner as in Example 1 by using the filter unit prepared by the above described method instead of the filter unit of Example 1.

To each of the two blood bags of the blood treating apparatus was fed 250 ml of CPD solution-added A type whole blood (hematocrit: 43%) from a healthy donor, and was stored for 21 days. Then, all the blood was allowed to flow through the filter unit from one of the blood bags and then the other at 25° C. by gravity caused by the head. Subsequently, 50 ml of a physiological saline was added and flowed by gravity to recover erythrocytes remaining in the filter unit. It took 9 minutes and 13 seconds for 500 ml of the stored blood to flow through the filter unit, and thus the flow rate was 54 ml/min. The number of microaggregates of altered blood components having at least 15 μm in size was 27,200 in 1 milliliter of the filtrate while the average number of the microaggregates contained in the stored blood in the two blood bags had been 3.41×10$^6$ per milliliter. Thus, the removal rate of microaggregates was 99.2%. The removal rate of leukocytes was 98.2% and the recovery rate of erythrocytes was 95.8%.

COMPARATIVE EXAMPLE 5

A filter unit was prepared in the same manner as in Example 6 except that the prefilters I to V were not used at all and the inside thickness of the container was 8 mm.

A blood treating apparatus was assembled in the samed manner as in Example 6 by using the filter unit thus prepared instead of the filter unit of Example 6.

To each of the two blood bags of the blood treating apparatus was fed 250 ml of the same stored blood as the one used in Example 6. Then, the blood was fed into the filter unit from one of the two blood bags and then the other at 25° C. by gravity caused by the head. After 41 minutes from the starting of the filtration and when 175 ml of the blood was fed into the filter unit, no filtrate could be obtained due to the clogging of the altered blood components contained in the stored blood.

EXAMPLE 7

A non-woven fabric having a bulk density of 0.18 g/cm$^3$ and an average distance between two adjacent fibers of 7.5 μm was prepared by spinning polyester fibers having a density of 1.38 g/cm$^3$ and an average diameter of 4.6 μm by the melt-blowing process, and entangling the fibers. Then, the non-woven fabric was cut out in the form of a disk having a diameter of 210 mm and a thickness of 0.25 mm, thereby to prepare a prefilter for removing altered blood components.

A non-woven fabric having a bulk density of 0.15 g/cm$^3$ and an average distance between two adjacent fibers of 1.3 μm was prepared by spinning polyester fibers having a density of 1.38 g/cm$^3$ and an average diameter of 0.7 μm by the melt-blowing process, and entangling the fibers. Then, the non-woven fabric was cut out in the form of a disk having a diameter of 210 mm and a thickness of 1.5 mm, thereby to prepare a main filter for entrapping and removing leukocytes.

A filter unit was prepared by placing the prefilter on the main filter, and fixing the piled filters in a container provided with an inlet conduit and an outlet conduit and having an inside thickness of 6 mm so as to face the prefilter to the inlet conduit and the main filter to the outlet conduit, respectively. The effective diameter of the filters was 200 mm.

By using the filter unit thus obtained, a blood treating apparatus was assembled in the same manner as in Example 1.

To each of the two blood bags of the blood treating apparatus was fed 200 ml of ACD-A solution-added A type whole blood (hematocrit: 35%) from a healthy donor, and was stored for 7 days. Then, all the blood was allowed to flow through the filter unit from one of the blood bags and then the other at 25° C. by gravity caused by the head. Subsequently, 190 ml of a physiological saline was added and flowed by gravity to recover erythrocytes remaining in the filter unit.

It took 4 minutes and 47 seconds for 400 ml of the stored blood to flow through the filter unit, and thus the flow rate was 84 ml/min. No microaggregate of altered blood components was found in the filtrate while the average number of the microaggregates at least 15 μm in size which had been contained in the stored blood in the two blood bags was 1.02×10$^6$ per milliliter. The removal rate of leukocytes was 99.6% and the recovery rate of erythrocytes was 86.6%.

COMPARATIVE EXAMPLE 6

A filter unit was prepared in the same manner as in Example 7 except that the prefilter was not used.

A blood treating apparatus was assembled in the same manner as in Example 7 by using the filter unit thus prepared instead of the filter unit of Example 7.

To each of the two blood bags of the blood treating apparatus was fed 200 ml of the same stored blood as the one used in Example 7. Then, the blood was fed into the filter unit from one of the blood bags and then the other at 25° C. by gravity caused by the head. After one hour and 30 minutes from the starting of the filtration and when 207 ml of the blood was fed into the filter unit, no filtrate could be obtained due to the clogging of altered blood components contained in the stored blood.

EXAMPLE 8

A thermally bonded non-woven fabric having a bulk density of 0.29 g/cm$^3$ (average distance between two adjacent fibers: 15.1 μm) and composed of polyester fibers having an average diameter of 14 μm and a density of 1.38 g/cm$^3$ was cut out in the form of a disk having a diameter of 130 mm and a thickness of 4 mm. This disk is referred to as prefilter I hereinafter.

A thermally bonded non-woven fabric having a bulk density of 0.22 g/cm$^3$ (average distance between two adjacent fibers: 7.1 μm) and composed of polypropylene fibers having an average diameter of 7.6 μm and a density of 0.91 g/cm³ was cut out in the form of a disk having a diameter of 130 mm and a thickness of 0.15 mm. This disk is referred to as prefilter II hereinafter.

A non-woven fabric having a bulk density of 0.18 g/cm³ and an average distance between two adjacent the fibers of 2.0 μm was prepared by spinning polyamide fibers (nylon 66) having a density of 1.14 g/cm³ and an average diameter of 1.4 μm by the melt-blowing process, entangling the fibers, and heating the entangled fibers at 250° C. for 0.5 seconds for bonding the contact points of the fibers. The non-woven fabric was cut out in the form of a disk having a diameter of 130 mm and a thickness of 3 mm, thereby to prepare a main filter for entrapping and removing leukocytes.

A filter unit was prepared by piling the main filter and the prefilters II and I on one another in this order, and fixing the piled filters in a container provided with an inlet conduit and an outlet conduit and having an inside thickness of 8 mm so as to face the prefilter I to the inlet conduit and the main filter to the outlet conduit, respectively. The effective diameter of the filter was 120 mm.

A blood treating apparatus was assembled in the same manner as in Example 1 by using the filter unit thus obtained.

CPD solution-added B type blood from a healthy donor was centrifuged to remove a small amount of plasma, thereby to prepare concentrated blood having a hematocrit of 64%. The concentrate blood was stored for 17 days and to each of the two blood bags of the blood treating apparatus was fed 200 ml of the blood. Then, the blood was allowed to flow through the filter unit from one of the blood bags and then the other at 25° C. by gravity caused by the head. Subsequently, 100 ml of a physiological saline was added and flowed by gravity to recover erythrocytes remaining in the filter unit.

It took 5 minutes and 16 seconds for 400 ml of the stored blood to flow through the filter unit, and thus the flow rate was 76 ml/min. The number of microaggregates of altered blood components at least 15 μm in size was 14,000 in 1 milliliters of the filrate while the average number of the microaggregates contained in the stored blood in the two blood bags had been $2.81 \times 10^6$ per milliliter. Thus, the removal rate of microaggregates was 99.5%. The removal rate of leukocytes was 98.8% and the recovery rate of erythrocytes was 91.8%.

COMPARATIVE EXAMPLE 7

A filter unit was prepared in the same manner as in Example 8 except that the prefilters I and II were not used and the inside thickness of the container was 7 mm.

By using the filter unit thus prepared, a blood treating apparatus was assembled in the same manner as in Example 8.

To each of the two blood bags of the blood treating apparatus was fed 200 ml of the same stored blood as the one used in Example 8. Then, the blood was fed into the filter unit from one of the blood bags and then the other at 25° C. by gravity caused by the head. After 50 minutes from the starting of the filtration and when 243 ml of the blood was fed into the filter unit, no filtrate could be obtained due to the clogging of altered blood components contained in the stored blood. The removal rate of leukocytes was 98.9%.

EXAMPLE 9

A non-woven fabric having a bulk density of 0.18 g/cm³ (average distance between two adjacent fibers: 52.4 μm) was prepared by adhering a mass of polyester fibers (density: 1.38 g/cm³) whose average diameter was 32 μm with resin. Then, the non-woven fabric was cut out in the form of a disk having a diameter of 90 mm and a thickness of 3 mm. This disk is referred to as prefilter I hereinafter.

A thermally bonded non-woven fabric having a bulk density of 0.20 g/cm³ (average distance between two adjacent fibers: 24.0 μm) and composed of polyester fibers (density: 1.38 g/cm³) having an average diameter of 16 μm was cut out in the form of a disk having a diameter of 90 mm and a thickness of 0.4 mm. This disk is referred to as prefilter II hereinafter.

A thermally bonded non-woven fabric having a bulk density of 0.25 g/cm³ (average distance between two adjacent fibers: 17.3 μm) and composed of polyester fibers (density: 1.38 g/cm³) having an average diameter of 14 μm was cut out in the form of a disk having a diameter of 90 mm and a thickness of 1.0 mm. This disk is referred to as prefilter III hereinafter.

A thermally bonded non-woven fabric having a bulk density of 0.31 g/cm³ (average distance between two adjacent fibers: 12.1 μm) and composed of polyester fibers (density: 1.38 g/cm³) having an average diameter of 12 μm was cut out in the form of a disk having a diameter of 90 mm and a thickness of 1.8 mm. This disk is referred to prefilter IV hereinafter.

A non-woven fabric having a bulk density of 0.35 g/cm³ and an average distance between two adjacent fibers of 2.3 μm was prepared by spinning polyester fibers having a density of 1.38 g/cm³ and an average diameter of 2.6 μm by the melt-blowing process, and entangling the fibers. Then, the non-woven fabric was cut out in the form of a disk having a diameter of 90 mm and a thickness of 4 mm, thereby to prepare a main filter for entrapping and removing leukocytes.

A filter unit was prepared by piling the main filter and the prefilters IV, III, II and I on one another in this order, and fixing the piled filters in a container provided with an inlet conduit and an outlet conduit and having an inside thickness of 15 mm so as to face the prefilter I to the inlet conduit and the main filter to the outlet conduit, respectively. The effective diameter of the filters was 80 mm.

By using the filter unit thus obtained, a blood treating apparatus was assembled by the same manner as in Example 1.

To each of the two blood bags of the blood treating apparatus was fed 250 ml of CPD solution-added B type whole blood (hematocrit: 38%) from a healthy donor, and was stored for 21 days. Then, all the blood was allowed to flow through the filter unit from one of the blood bags and then the other at 10° C. by gravity caused by the head. Subsequently, 90 ml of a physiological saline was added and flowed by gravity to recover erythrocytes remaining in the filter unit.

It took 7 minutes and 56 seconds for 500 ml of the stored blood to flow through the filter unit, and thus the flow rate was 63 ml/min. The number of microaggregates of altered blood components at least 15 μm in size was 42,200 in 1 milliliter of the filtrate while the average number of the microaggregates contained in the stored blood in the two blood bags had been $3.52 \times 10^6$ per milliliter. Thus, the removal rate of microaggregates was 98.8%. The removal rate of leukocytes was 97.6% and the recovery rate of erythrocytes was 95.1%.

COMPARATIVE EXAMPLE 8

A filter unit was prepared in the same manner as in Example 9 except that the prefilters I to IV were not used and the inside thickness of the container was 8 mm.

By using the filter unit thus prepared, a blood treating apparatus was assembled in the same manner as in Example 9.

To each of the two blood bags of the blood treating apparatus was fed 250 ml of the same stored blood as the one used in Example 9. Then, the blood was fed into the filter unit from one of the blood bags and then the other at 10° C. by gravity caused by the head. After 53 minutes from the starting of the filtration and when 189 ml of the blood was fed into the filter unit, no filtrate could be obtained due to the clogging of altered blood components contained in the stored blood.

What is claimed is:

1. A method for removing leukocytes from a leukocyte-containing suspension, comprising the steps of: passing a leukocyte-containing suspension through a filter unit which comprises:
   a container having at least one inlet conduit means and at least one outlet conduit means; and
   a main filter packed therein in the form of a nonwoven fabrics, said fabrics comprising fibers wherein the average daimeter of all of the fibers in said fabrics is from 0.3 μm to less than 3 μm and said fabric having a bulk density of from 0.01 g/cm³ to 0.7 g/cm³, and wherein the average distance between any two of all adjacent fibers throughout said fabric is 0.5 μm to 7.0 μm and is defined by the following equation (1):

$$y = x \left( \sqrt{\frac{\pi}{2\sqrt{3}}} \cdot \sqrt{\frac{\rho}{D}} - 1 \right) \quad (1)$$

wherein y is the average distance between two adjacent fibers in microns; x is the average diameter of fibers in microins; ρ is the density of the fibers in g/cm³; D is the bulk density of the filter in g/cm³; and π is a circular constant; and
obtaining a leukocyte-poor liquid.

2. A method for removing leukocytes from a leukocyte-containing suspension, comprising the steps of: passsing a leukocyte-containing suspension through a filter unit which comprises:
   a container having at least one inlet conduit means and at least one outlet conduit means; and
   a main filter packed therein in the form of a nonwoven fabric, said fabric comprising fibers wherein the average diameter of all of the fibers in said fabric is from 0.3 μm to less than 3 μm and said fabric having a bulk density of from 0.01 g/cm³ to 0.7 g/cm³, and wherein the average distance between any two of all adjacent fibers throughout said fabric is 0.5 μm to 7.0 μm and is defined by the following equation (1):

$$y = x \left( \sqrt{\frac{\pi}{2\sqrt{3}}} \cdot \sqrt{\frac{\rho}{D}} - 1 \right) \quad (1)$$

wherein y is the average distance between two adjacent fibers in microns; x is the average diameter of fibers in microns; ρ is the density of the fibers in g/cm³; D is the bulk density of the filter in g/cm³; and π is a circular constant;
separating out storage generated microaggregates and adhesive substance with a prefilter inserted in the container between the inlet conduit means and the main filter; and obtaining a leukocyte-poor liquid.

* * * * * ive
REEXAMINATION CERTIFICATE (2811th)
United States Patent [19]

Watanabe et al.

[11] B1 4,701,267

[45] Certificate Issued   Mar. 12, 1996

[54] METHOD FOR REMOVING LEUKOCYTES

[75] Inventors: Hiroyuki Watanabe; Hiroshi Rikumaru, both of Oita, Japan

[73] Assignee: Asahi Medical Co., Ltd., Tokyo, Japan

Reexamination Request:
No. 90/003,726, Feb. 16, 1995

Reexamination Certificate for:
Patent No.: 4,701,267
Issued: Oct. 20, 1987
Appl. No.: 711,667
Filed: Mar. 14, 1985

[30]     Foreign Application Priority Data

Mar. 15, 1984 [JP] Japan .................. 59-48173
Mar. 27, 1984 [JP] Japan .................. 59-57450

[51] Int. Cl.$^6$ .............. B01D 27/02; B01D 36/02; B01D 39/02; A61M 37/00
[52] U.S. Cl. .............. 604/5; 210/335; 210/491; 210/492; 210/505; 210/806; 604/4
[58] Field of Search ............. 210/335, 446, 210/451, 489, 491, 492, 929, 767, 806, 295, 314, 503, 504, 505, 508, 509; 55/512, 527; 604/4, 5, 6

[56]                References Cited

U.S. PATENT DOCUMENTS

| | | | |
|---|---|---|---|
| 3,003,643 | 10/1961 | Thomas | 210/491 |
| 3,593,854 | 7/1971 | Swank | 210/436 |
| 4,009,715 | 3/1977 | Forberg et al. | 210/455 |
| 4,073,732 | 2/1978 | Laurer et al. | 210/491 |
| 4,191,654 | 3/1980 | Larson | 210/451 |
| 4,229,306 | 10/1980 | Hein et al. | 210/451 |
| 4,246,107 | 1/1981 | Takenaka et al. | 210/806 |
| 4,283,289 | 8/1981 | Meyst et al. | 210/450 |
| 4,294,594 | 10/1981 | Sloane, Jr. et al. | 210/446 |
| 4,330,410 | 5/1982 | Takenaka et al. | 210/767 |
| 4,342,730 | 8/1982 | Perrotta | 210/509 |
| 4,376,675 | 3/1983 | Perrotta | 210/509 |
| 4,447,575 | 4/1992 | Vogel et al. | 436/170 |
| 4,608,173 | 8/1986 | Watanabe et al. | 210/508 |
| 4,816,224 | 3/1989 | Vogel et al. | 422/55 |

FOREIGN PATENT DOCUMENTS 53-24454  9/1479  Japan .
53-24458  9/1979  Japan .

OTHER PUBLICATIONS

Ullmanns Encyclopädie der technischen Chemie, 4th ed. vol. 23, pp. 729–730, 1983 Verlag Chemie (Weinheim—Dearfield Beach FL—Basel) and English Translation thereof.

"Evaluation of a New Filter for Leucocyte Depletion of Blood" by Johnson, J., et al., Oct. 1983, J.Clin.Pathology 36:1200.

*Primary Examiner*—John Kim

[57]               ABSTRACT

A filter unit for removing leukocytes from a leukocyte-containing suspension, comprising a container provided which at least one inlet conduit means and at least one outlet conduit means, the container having a main filter packed therein in the form of a non-woven fabric which comprises fibers of an average diameter of from 0.3 μm to less than 3 μm and which has a bulk density of from 0.01 g/cm$^3$ to 0.7 g/cm$^3$, and which has an average distance between two adjacent fibers defined by the following equation (1) of from 0.5 μm to 7.0 μm:

$$y = x \left( \sqrt{\frac{\pi}{2\sqrt{3}}} \cdot \sqrt{\frac{\rho}{D}} - 1 \right) \quad (1)$$

wherein y is the average distance between two adjacent fibers in micron; x is the average diameter of fibers in microns; ρ is the density of the fibers in g/cm$^3$; D is the bulk density of the filter in g/cm$^3$; and π is a circular constant.

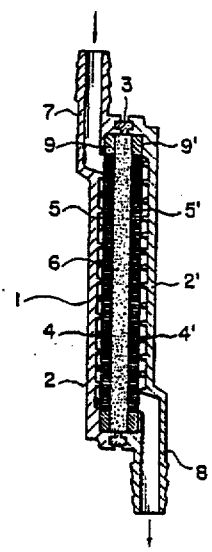

B1 4,701,267

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–2 is confirmed.

New claims 3–6 are added and determined to be patentable.

3. *A method of treating a patient which comprises the steps of claim 1 or 2, wherein the leukocyte-containing suspension is further comprised of a non-leukocyte blood component, and wherein the method further comprises the steps of tranfusing a patient in need of the blood component with the leukocyte-poor liquid, which is comprised of the blood component.*

4. *The method of claim 3 wherein the thickness of the non-woven fabric of the main filter unit is between about 1.0 mm and about 20.0 mm and the area of the surface of the main filter unit is 10 $cm^2$ to 1000 $cm^2$.*

5. *The method of claim 3 wherein the leukocyte-containing suspension and the leukocyte-poor fluid are comprised of erythrocytes.*

6. *The method of claim 5 wherein the thickness of the non-woven fabric of the main filter unit is between about 1.0 mm and about 20.0 mm and the area of the surface of the main filter unit is 10 $cm^2$ to 1000 $cm^2$ and the volume of the leukocyte-containing suspension is greater than about 200 milliliters.*

\* \* \* \* \*